US010773691B2

(12) United States Patent
Schutz (10) Patent No.: US 10,773,691 B2
(45) Date of Patent: Sep. 15, 2020

(54) BIOLOGICAL SECURITY VEHICLE WASHING APPARATUS AND METHOD

(71) Applicant: Jeffrey Allen Schutz, Alexandria, MN (US)

(72) Inventor: Jeffrey Allen Schutz, Alexandria, MN (US)

(*) Notice: Subject to any disclaimer, the term of this patent is extended or adjusted under 35 U.S.C. 154(b) by 124 days.

(21) Appl. No.: 16/151,947

(22) Filed: Oct. 4, 2018

(65) Prior Publication Data

US 2019/0106087 A1  Apr. 11, 2019

Related U.S. Application Data

(60) Provisional application No. 62/568,615, filed on Oct. 5, 2017.

(51) Int. Cl.
| | | |
|---|---|---|
| *A61L 2/18* | (2006.01) | |
| *A61L 2/24* | (2006.01) | |
| *B60S 3/04* | (2006.01) | |
| *A61L 9/14* | (2006.01) | |

(52) U.S. Cl.
CPC . *B60S 3/04* (2013.01); *A61L 2/18* (2013.01); *A61L 2/24* (2013.01); *A61L 9/14* (2013.01); *A61L 2202/15* (2013.01); *A61L 2202/16* (2013.01)

(58) Field of Classification Search
CPC ..... A61L 2/18; A61L 2/24; A61L 9/14; A61L 2202/15; A61L 2202/16; A61L 2202/17; B60S 3/04; B60S 3/042; B60S 3/047
See application file for complete search history.

(56) References Cited

U.S. PATENT DOCUMENTS

| | | | |
|---|---|---|---|
| 2,981,266 | A | 4/1961 | Tamburri |
| 3,072,131 | A | 1/1963 | Laurenzio |
| 3,258,019 | A | 6/1966 | Bellas et al. |
| 3,698,029 | A | 10/1972 | Pulliam |
| 6,358,330 | B1 | 3/2002 | McGraw |

(Continued)

FOREIGN PATENT DOCUMENTS

| | | |
|---|---|---|
| CN | 101773679 A | 7/2010 |
| CN | 102397044 A | 4/2012 |

(Continued)

OTHER PUBLICATIONS

Wiebe Van Der Sluis, "Automatic vehicle disinfection", World Poultry, vol. 20, No. 12, 2004, 2 pages.

(Continued)

*Primary Examiner* — Lessanework Seifu
(74) *Attorney, Agent, or Firm* — Patterson Thuente Pedersen, P.A.

(57) ABSTRACT

An automatic vehicle disinfection system for promoting biosecurity through application of a disinfectant to a vehicle transiting to and from an agricultural site or the like. The automatic vehicle disinfection system includes a pair of resilient drums, each drum including a riser tube having one or more disinfectant dispensing nozzles, and at least one of the drums further including a disinfectant reservoir, a resilient cross tube fluidly connecting the riser tubes and including a central spray unit having one or more disinfectant dispensing nozzles, a pressure pump configured to pump disinfectant from the disinfectant reservoir to the disinfectant dispensing nozzles, and a control assembly including a pressure pump activation trigger configured to activate the pressure pump.

15 Claims, 9 Drawing Sheets

(56) References Cited

U.S. PATENT DOCUMENTS

| | | | |
|---|---|---|---|
| 6,568,411 B1 | 5/2003 | Staples et al. | |
| 7,775,221 B2 | 8/2010 | Zeile | |
| 8,858,878 B2 | 10/2014 | Risch et al. | |
| 2003/0233153 A1 | 12/2003 | Grier | |
| 2004/0231703 A1 | 11/2004 | McCormick et al. | |
| 2005/0073133 A1 | 4/2005 | Dufty | |
| 2006/0157094 A1 | 7/2006 | Zelle | |
| 2010/0219039 A1 | 9/2010 | Ringdahl et al. | |
| 2012/0012138 A1 | 1/2012 | Garrett | |
| 2014/0102489 A1 | 4/2014 | Smith | |
| 2014/0158794 A1 | 6/2014 | Wilkinson | |
| 2014/0224279 A1 | 8/2014 | Anderson | |
| 2016/0311409 A1 | 10/2016 | Schutz | |

FOREIGN PATENT DOCUMENTS

| | | |
|---|---|---|
| CN | 204092639 U | 1/2015 |
| DE | 10208926 A1 | 9/2003 |
| EP | 1911643 A1 | 4/2008 |
| GB | 2362617 A | 11/2001 |
| GB | 2377879 A | 1/2003 |
| KR | 101173263 B1 | 8/2012 |
| WO | WO 01/15824 A1 | 3/2001 |
| WO | WO 2011/104478 A1 | 9/2011 |
| WO | WO 2012/083316 A2 | 6/2012 |

OTHER PUBLICATIONS

Luc Ledoux, "Vehicle Biosecurity in Poultry Production", The Poultry Site, Feb. 4, 2007, 3 pages.

"Interim Guidance for Protection of Persons Involved in U.S. Avian Influenza Outbreak Disease Control and Eradication Activities", Centers for Disease Control and Prevention, Jan. 14, 2006, 3 pages.

Search Report and Written Opinion dated Aug. 18, 2016 for PCT Application No. PCT/US16/28621, 14 pages.

BIOLOGICAL SECURITY VEHICLE WASHING APPARATUS AND METHOD

RELATED APPLICATION

The present application claims the benefit of U.S. Provisional Application No. 62/568,615 filed Oct. 5, 2017, which is hereby incorporated herein in its entirety by reference.

TECHNICAL FIELD

The present disclosure relates generally to drive-over vehicle tire and undercarriage sanitizing systems. More particularly, the present disclosure relates to methods and systems for promoting safety and reducing contamination in vehicles after having transported or passed through areas potentially contaminated with a biological security threat.

BACKGROUND

Avian influenza virus outbreaks over the recent years have put the application of current bio-security practices into question. One of the identified vectors for spreading the disease is the so called "mobile vector," caused by vehicles and people moving into and out of areas where poultry is raised and processed. It is believed that more rigorous practices of vehicle hygiene will aid in the curtailing of future outbreaks.

Avian influenza viruses are influenza viruses that primarily infect birds, including poultry such as turkeys and chickens. Avian influenza viruses are type A influenza viruses that are genetically distinguishable from influenza viruses that usually infect people. There are many subtypes of avian influenza A viruses, including H7 and H5. Avian influenza viruses can be distinguished as "low pathogenic" and "high pathogenic" forms based on genetic features of the virus and the severity of the illness they cause in poultry.

Birds that are infected with avian influenza viruses are known to spread the virus through saliva, nasal secretions, and feces. Contact with feces or respiratory secretions may lead to the transmission of infection among poultry. Between flocks, infection usually spreads due to movement of infected birds and the actions of humans in moving feedstuff, personnel, equipment, and vehicles into and from premises that are contaminated with infected feces or respiratory secretions.

Infection among poultry often proves fatal and has the potential to decimate an entire flock within days. Even if not fatal, typically all other birds in proximity to the infected birds are destroyed for preventative measures. Further, given that the viruses can survive in many environments for weeks, federal and state regulations often prohibit the infected facilities from being reused for at least one month or more. This loss and delay can represent a serious financial toll on poultry growers and processors.

Over the years, various organizations have recommended that poultry growers improve their vehicle hygiene practices. Typically these practices involve maintaining separate traffic routes, so that only essential vehicles are permitted access to areas where birds are kept, as well as disinfecting the wheels and undercarriage of any vehicles entering these areas.

However, effectively disinfecting vehicles according to the recommended practices has been difficult to achieve. Commonly, hand-held spraying systems are employed to apply disinfectant to vehicles. However, applying disinfectant through such a method can lead to non-uniform application; particularly to portions of the under carriage of the vehicle where application of disinfectant can be altogether missed. Non-uniformity in application can be even more prevalent when it is left up to drivers, with varying levels of biosecurity training, to disinfect their own vehicles. Moreover, proper disinfection of vehicles through these methods can be very time consuming.

Recently, Applicants of the present disclosure have developed mobile vehicle wash systems configured to provide a level of automation to more uniformly apply disinfectant to vehicles, including the undercarriage of vehicles, in an efficient and effective manner. An example of this type of mobile vehicle wash system is disclosed in U.S. Patent Publ. No. 20160311409, filed Apr. 21, 2016, the disclosure of which is hereby incorporated by herein by reference in its entirety. These affordable and highly mobile systems have greatly improved the availability of automated disinfectant wash vehicle systems to poultry farmers. It is believed that through their continued use, any future spread of the avian flu virus within the poultry industry, particularly one spread by the mobile vector, can be significantly curtailed.

Although such systems provide a significant advantage over the prior art, and are priced at a fraction of the cost of automatic carwashes and wheel baths, their cost can still present an obstacle to small-and medium-sized poultry farms. Moreover, despite being modular and highly mobile on a farm site, the cost of shipping such systems across the country and internationally can present a significant additional expense. It has additionally been noted that careless drivers and drivers unaware of the width of their vehicle can inadvertently run into portions of the mobile vehicle wash systems, thereby damaging the systems and rendering them inoperable. The present disclosure addresses these concerns.

SUMMARY OF THE DISCLOSURE

Embodiments of the present disclosure meet the need of the industry for an affordable, easy to ship, mobile system for disinfecting vehicles to promote improved bio-security that is resistive to damage caused by careless drivers and vehicles bumping into portions of the system. In one embodiment, the system enables the automatic application of disinfectant in a quantity recommended by the manufacturer substantially uniformly across the wheels and undercarriage of the vehicle. In one embodiment, the system requires minimal user interaction to reduce the likelihood of introducing human error during the application of disinfectant. In one embodiment, the system is portable or semi-portable, so that the system can be redeployed or readily moved from one location to another location in a short period of time. In one embodiment, the cost of the system is priced so that small-and medium-sized poultry farms can afford to purchase and install the system, thereby promoting more widespread bio-security practices across the agricultural industry.

One embodiment of the present disclosure provides a mobile vehicle disinfection system for promoting bio-security through the application of a disinfectant to a vehicle transiting to and from an agricultural site. The automatic vehicle disinfection system can include a pair of resilient drums, each drum including a riser tube having one or more disinfectant dispensing nozzles, and at least one of the drums further including a disinfectant reservoir. The automatic vehicle disinfection system can include resilient cross tube fluidly connecting the riser tubes and including a central spray unit having one or more disinfectant dispensing nozzles. The automatic vehicle disinfection system can include a pressure pump configured to pump disinfectant from the disinfectant reservoir to the disinfectant dispensing nozzles, and the automatic vehicle disinfection system can include a control assembly including a pressure pump activation trigger configured to activate the pressure pump.

In one embodiment, the disinfectant reservoir can be heated to promote the free flow of disinfectant and inhibit the disinfectant from freezing or from having ice crystals formed therein.

In one embodiment, the cross tube can be variable in length and/or easily interchangeable, so as to accommodate vehicles in a range of widths and sizes.

In one embodiment, the pair of resilient drums can be configured to resist damage when impacted by a vehicle. For example, the resilient drums can be constructed of a resilient rubber or plastic material, configured to temporarily deform and resume their original shape after being impacted by an external force. In one embodiment, the riser tubes and/or the cross tube can be constructed of a resilient hose member configured to deform upon the application of stress, thereby inhibiting damage from fracturing upon impact.

In one embodiment, the mobile vehicle disinfection system can be collapsed down and packed into at least one of the pair of resilient drums, thereby significantly reducing its bulk and the associated costs with shipping.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIGS. 6A-7 are perspective views depicting a control assembly in accordance with an embodiment of the disclosure.

While embodiments of the disclosure are amenable to various modifications and alternative forms, specifics thereof are shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION

Figure 1A:
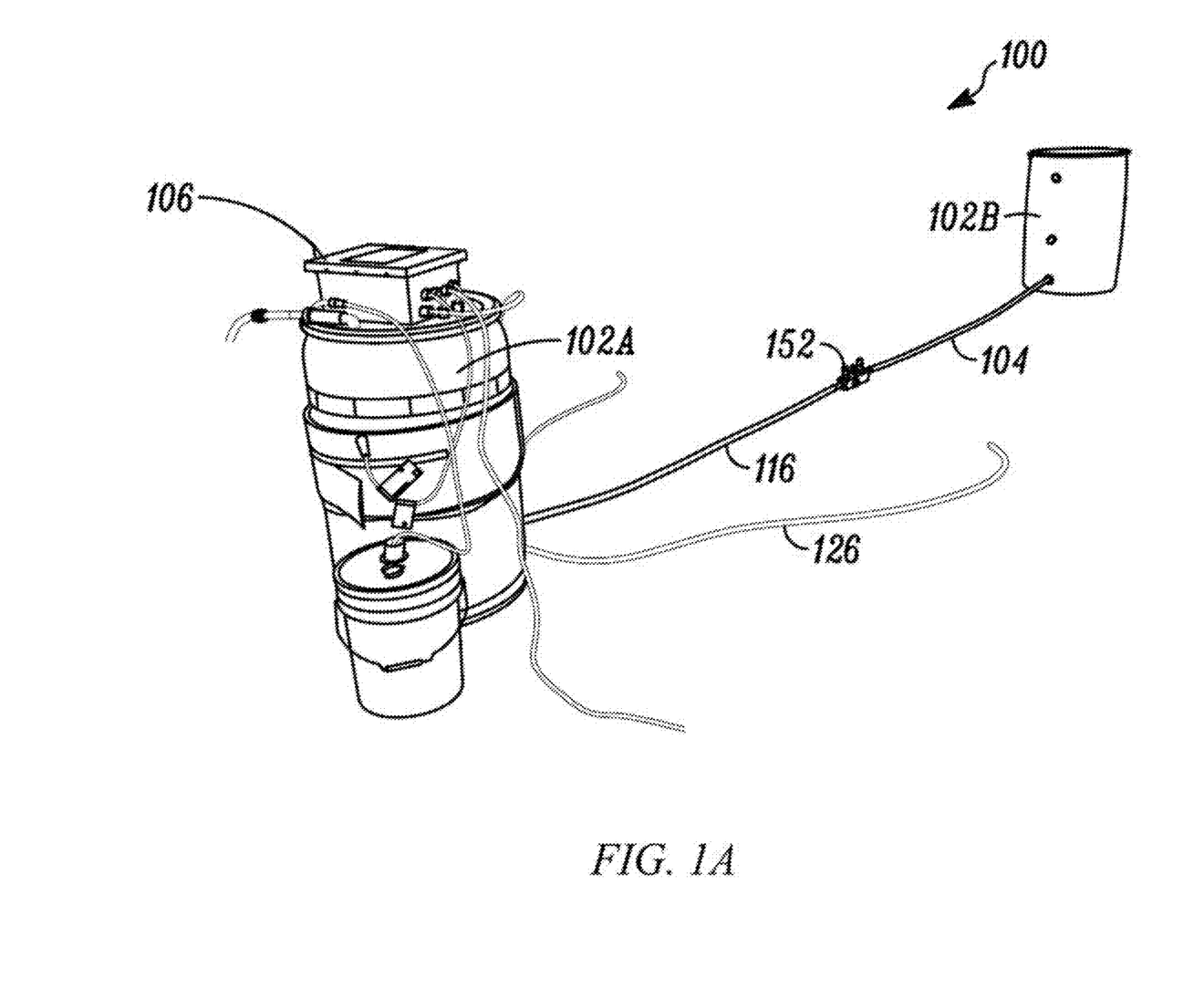
FIGS. 1A-1B are perspective views depicting an automatic vehicle disinfection station in accordance with an embodiment of the disclosure.
Figure 1B:
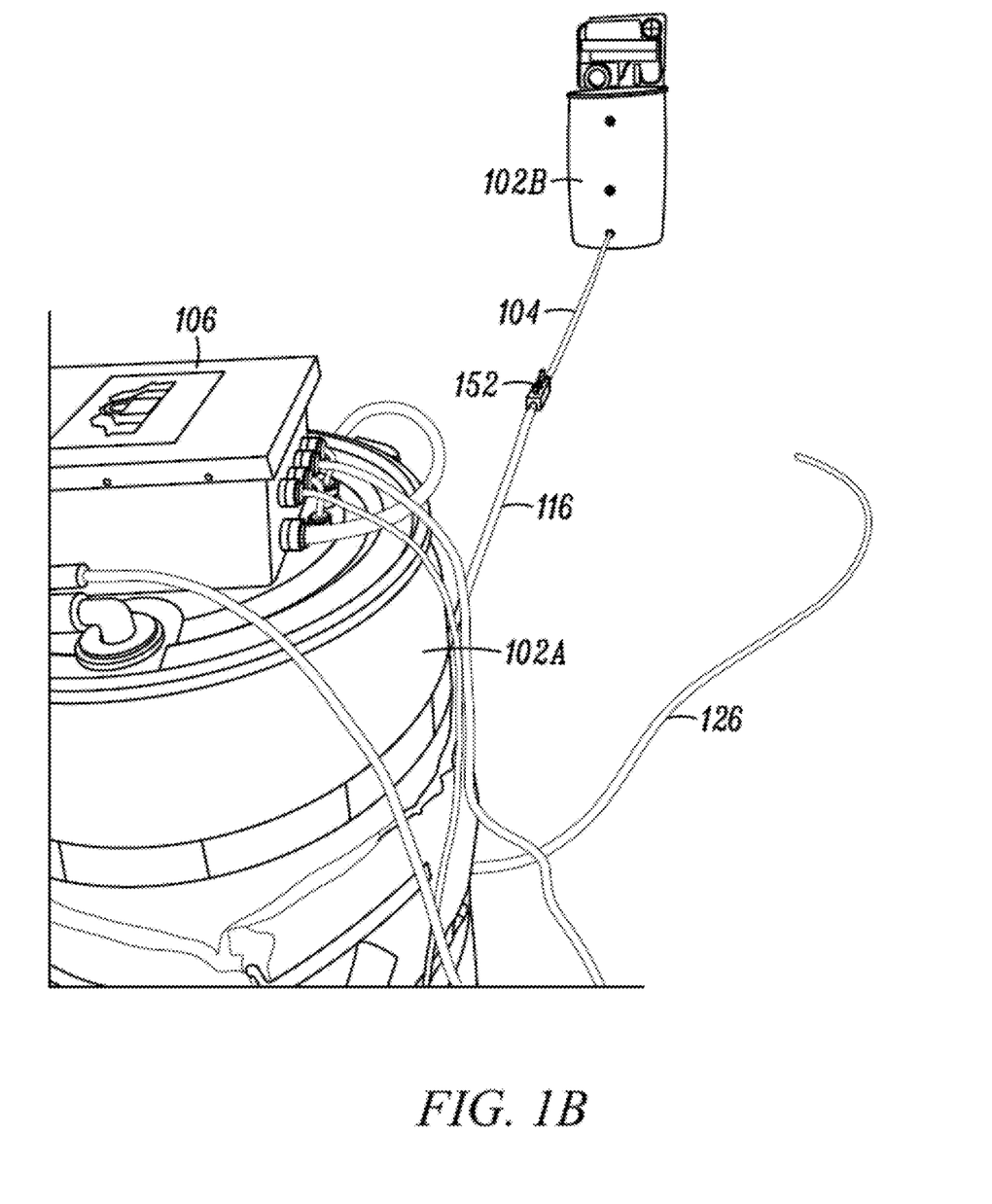

Referring to FIGS. 1A-B, an automatic vehicle disinfection station 100 is depicted in accordance with an embodiment of the disclosure. Automatic vehicle disinfection station 100 generally includes a first resilient drum 102A, a second resilient drum 102B, a disinfectant supply system 104, and a control system 106.

In one embodiment, the first and second resilient drums 102A/B are configured to resist damage when impacted by a vehicle. For example, the resilient drums 102 can be commercially available fifty-five gallon drums constructed of a resilient rubber or plastic material, configured to temporarily deform and resume their original shape after being impacted by a vehicle. In some embodiments, reflective signage can be affixed to an exterior surface of the resilient drum.

Figure 2:
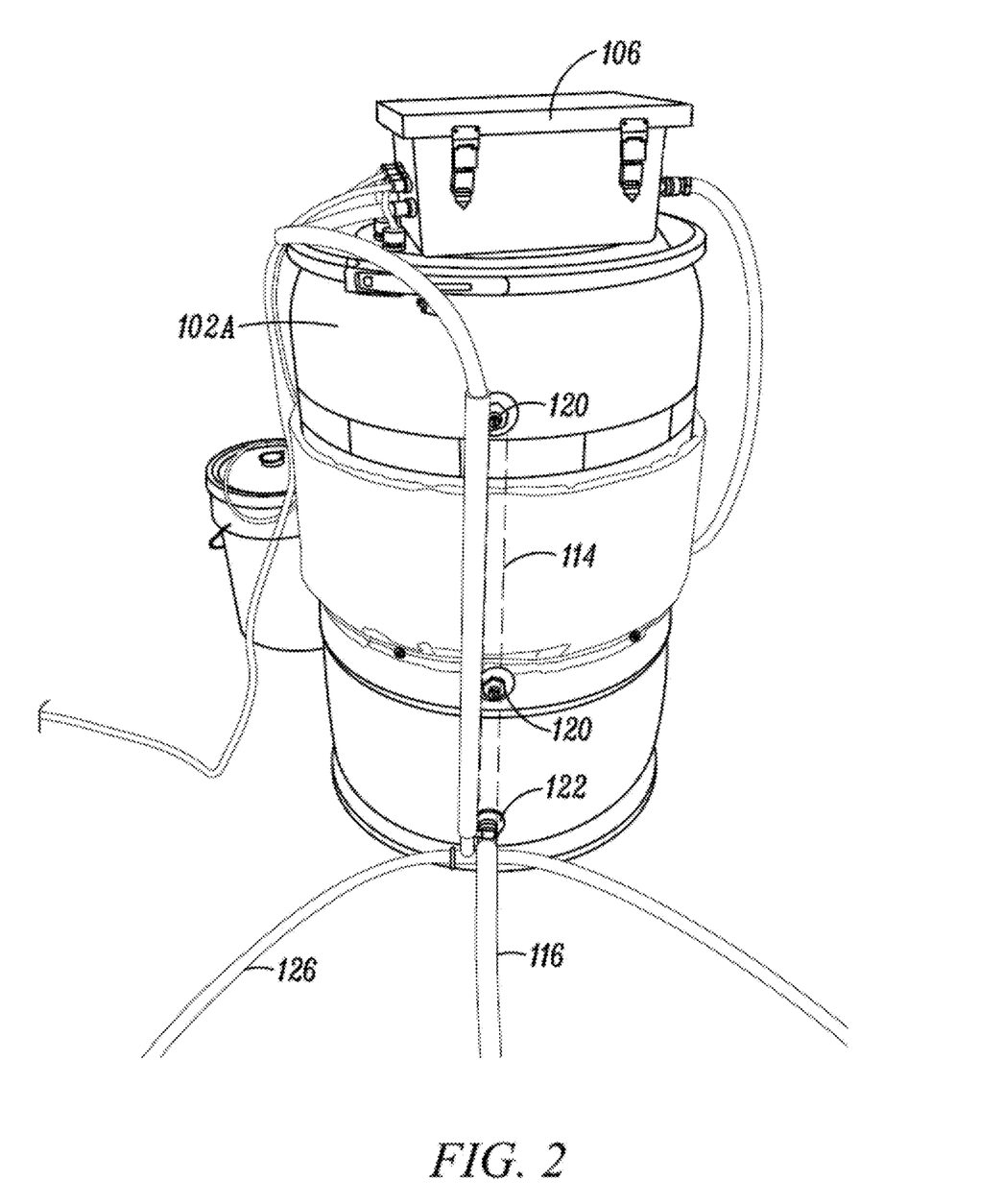
FIG. 2 is a perspective view depicting a first resilient drum in accordance with an embodiment of the disclosure.
Figure 3:
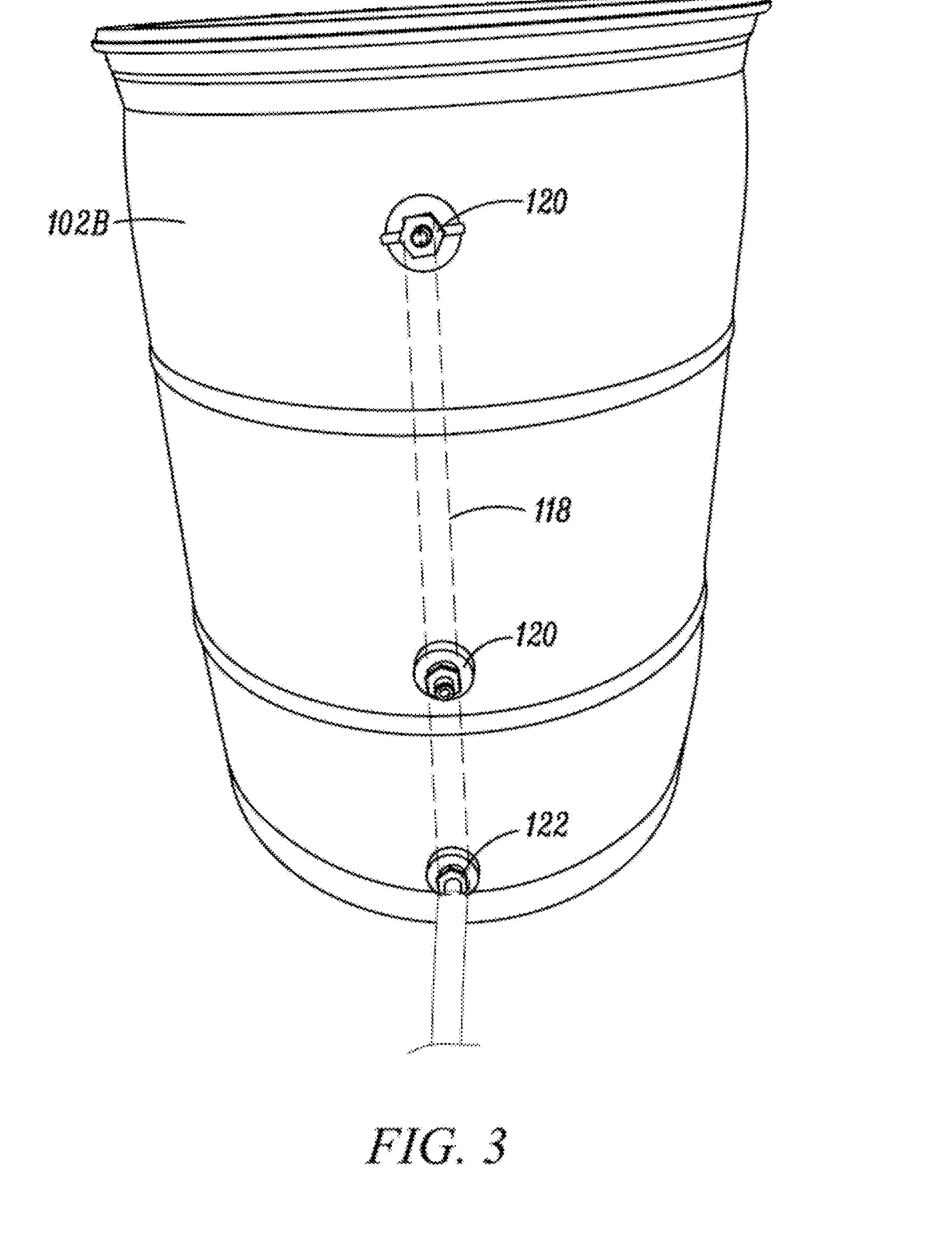
FIG. 3 is a perspective view depicting a second resilient drum in accordance with an embodiment of the disclosure.

In one embodiment, the disinfectant supply system 104 can include a pressure pump 113, in fluid communication with a first riser tube 114, one or more cross tubes 116, and a second riser tube 118. In one embodiment, the first riser tube 114 and second riser tube 118 are in fluid communication with one another by at least one cross tube 116. In one embodiment, riser tubes 114 and 118 are operably coupled to the respective first and second resilient drums 102A/B. For example, as depicted in FIGS. 2-3, the riser tube 114/116 can be positioned on the inside of resilient drum 102, such that only dispensing nozzles 120 in fluid communication with the riser tubes 114/116 protrude from the outer surface of the resilient drums 102A/B.

In some embodiments, there can be more than two cross tubes and the risers can be in other configurations. For example, there can be more than two risers to accommodate more than a single lane of traffic or vehicle at a given time. In one embodiment, the one or more cross tubes 116 can be constructed of a flexible, or semi-flexible material to allow for deformations as vehicles pass over the one or more cross tubes 116, thereby inhibiting damage or fracturing upon impact by a vehicle. Additionally, the flexible or semi-flexible cross tubes 116 can enable either of the resilient drums 102 to be moved, for example if inadvertently bumped with a vehicle, thereby enabling drum 102 to slide across the ground without causing the cross tube 116 to fracture.

In one embodiment, the one or more cross tubes 116 can reside within a rubber drive over ramp. Each rubber drive over ramp can be configured to enable a vehicle to smoothly transition over the one or more cross tubes 116 and back to the ground. In one embodiment, rubber drive over ramps can be between one and four inches in height, and serve as a "speed bump," thereby causing vehicles to slow as they pass over the ramps. The rubber drive over ramp can include one or more channels formed therein, wherein the channels can be configured to receive a portion of the disinfectant supply system 104.

In one embodiment, the various sections of the disinfectant supply system 104, for example the various cross tubes 116, and riser tube 114, 118 can be coupled to one another by quick disconnect couplings 122, thereby enabling vehicle disinfection station 100 to be more easily assembled and disassembled. In one embodiment, quick disconnect couplings 122 can be threaded couplings. In another embodiment, quick disconnect couplings 122 can be snap fit couplings. Quick disconnect couplings 122 can greatly improve functionality of the vehicle disinfection system 100 by reducing the amount of time in which the vehicle disinfection system 100 can be assembled and disassembled to promote mobility, as well as enable various portions of the disinfectant supply system 104 to be replaced with greater ease.

The riser tubes 114 and 118, and cross tube 116 can include a plurality of disinfectant dispensing nozzles 120. In one embodiment, the dispensing nozzles 120 are evenly spaced across riser tubes 114 and 118, and cross tube 116 over the span of the width of the vehicle, thereby enabling both left and right tires and undercarriage surfaces to be properly sanitized. In other embodiments, dispensing nozzles 120 are spaced in a manner that provides more coverage to areas of the vehicle most likely to be in contact with bio-hazardous material. In one embodiment, a plurality of dispensing nozzles 120 are configured in a variety of locations at different angles thereby enabling all surfaces of the vehicle to receive ample coverage of disinfectant. In one embodiment, dispensing nozzles 120 are configured to dispense disinfectant to the wheel inners, outers, treads, wheel arches, undercarriage, front, rear, sides, and roof top (optional). In one embodiment, dispensing nozzles 120 disperse disinfectant at a wide pattern angle, such as a pattern angle between ten and sixty degrees. In one embodiment, the dispensing nozzles 120 pattern angle is approximately forty degrees. In one embodiment, at least a portion of the cross tube 116 at least partially resides in a channel of the rubber drive over ramp, thereby protecting the dispensing nozzles 120 from inadvertent damage from vehicles.

Figure 4:
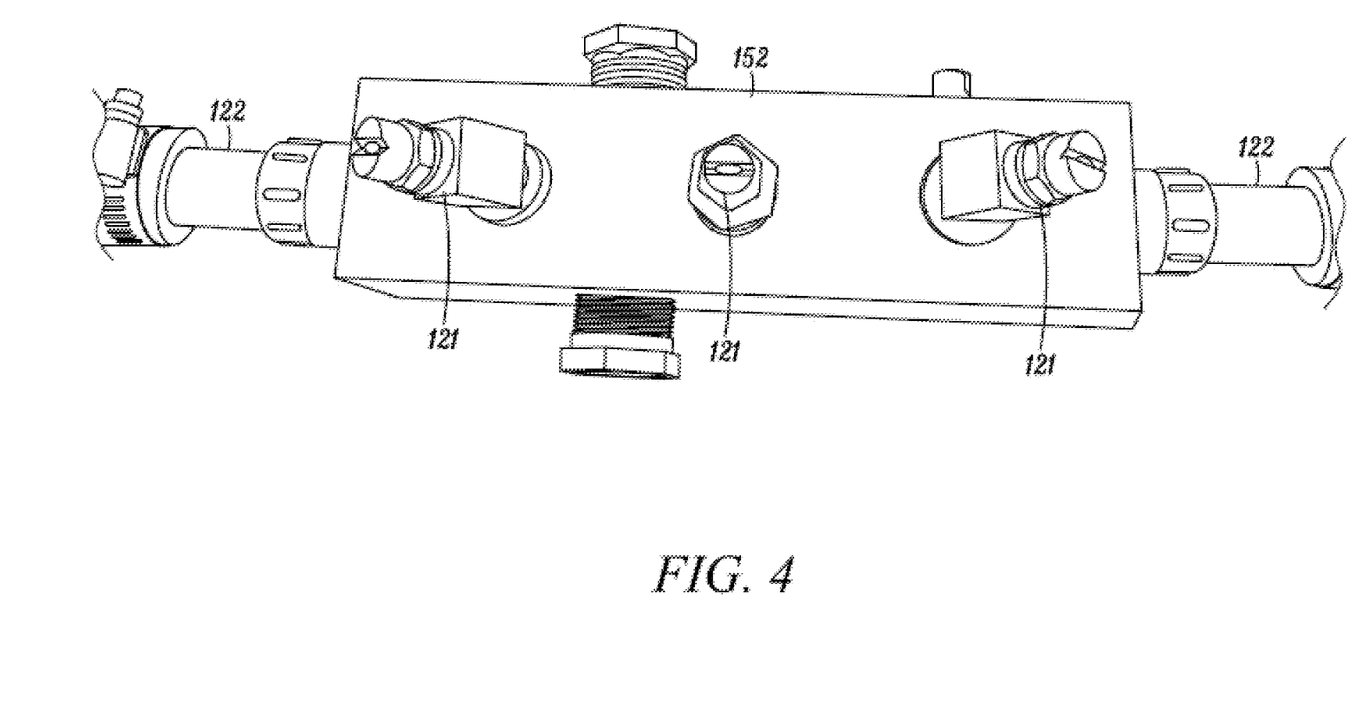
FIG. 4 is a perspective view depicting a central spray unit in accordance with an embodiment of the disclosure.

Referring to FIG. 4, in one embodiment, the one or more cross tubes 116 include a central spray unit 152. Central spray unit 152 can include a plurality of nozzles 121 configured to dispense a disinfectant solution to the undercarriage of a vehicle in an array of patterns, such as between ninety and one hundred eighty degrees. In some embodiments, the nozzles 121 of central spray unit 152 can be countersunk to inhibit inadvertent damage from vehicles.

In one embodiment, the disinfectant supply system 104 further includes a disinfectant reservoir 105 configured to store a disinfecting agent or components thereof. The disinfectant reservoir 105 can, in some embodiments, be positioned within the first and/or second resilient drum 102A/B. For example, in one embodiment, the resilient drum 102 can itself serve as the disinfectant reservoir. The disinfectant reservoir can include a heater or agitator configured to promote the free flow of disinfectant fluid throughout the disinfectant supply system 104 by inhibiting the growth of ice crystals within the disinfectant and/or inhibiting the disinfectant from increasing in viscosity and/or freezing. Such heaters and/or agitators can be in communication with a temperature sensor or other environmental sensor, so that the heater and/or agitator only become operational during certain environmental conditions, such as a low temperature. In some embodiments, the heater and/or agitator can be on a timed cycle, so that the heater and/or agitator cycles on and off according to a predetermined time or formula.

Figure 5:
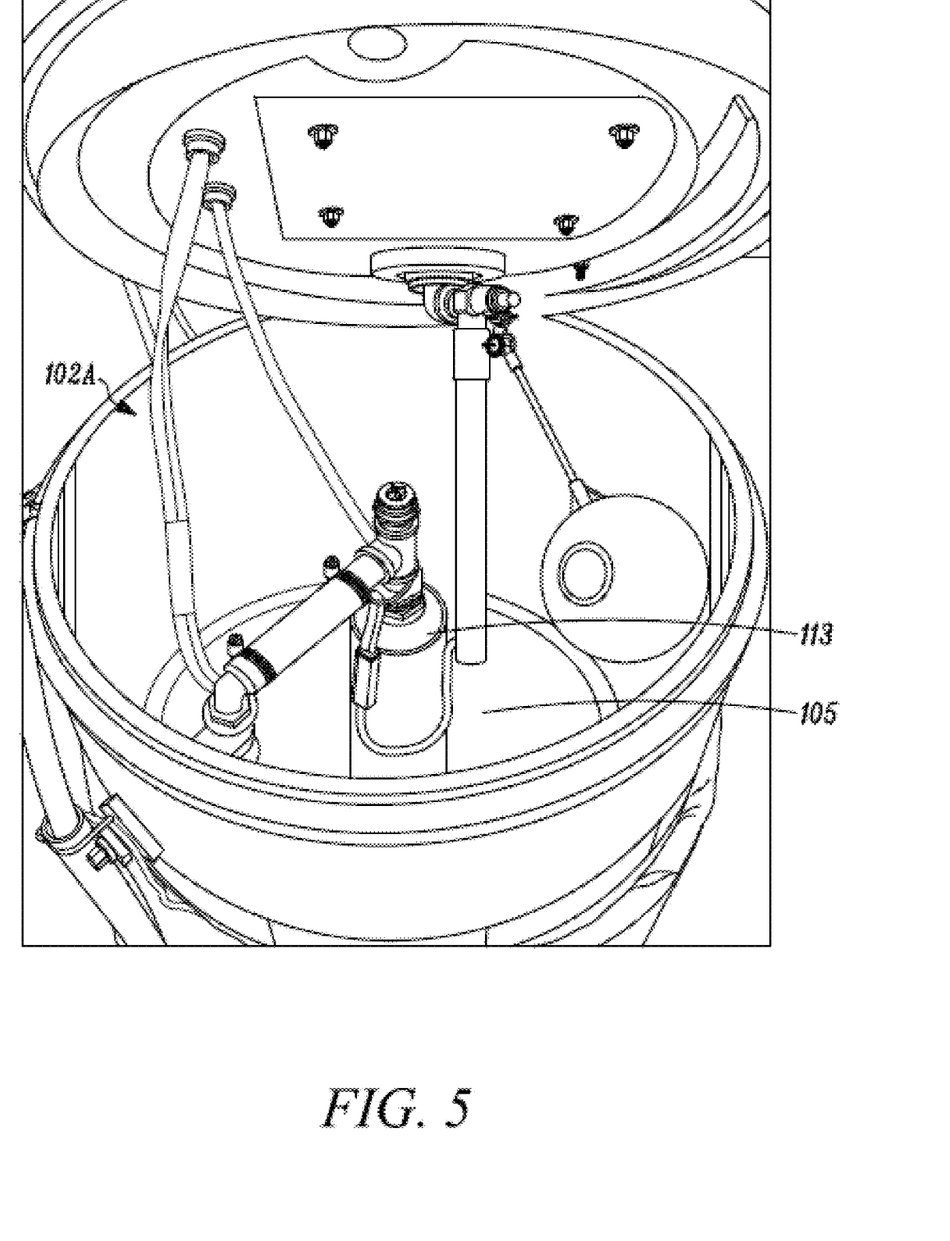
FIG. 5 is a perspective view depicting a pressure pump and disinfectant reservoir in accordance with an embodiment of the disclosure.

Referring to FIG. 5, the pressure pump 113 of the disinfectant supply system 104 can be a high pressure pump configured to boost the pressure of the disinfectant sufficiently to enable delivery of the required amount of disinfectant in the amount prescribed by the manufacturer of the disinfectant over a time period, for example, in a time of less than one minute. The pressure pump 113 can be positioned within the resilient drum 102. For example, in one embodiment, the pressure pump 113 can be a submersible pump positioned within the disinfectant reservoir 105.

Figure 6A:
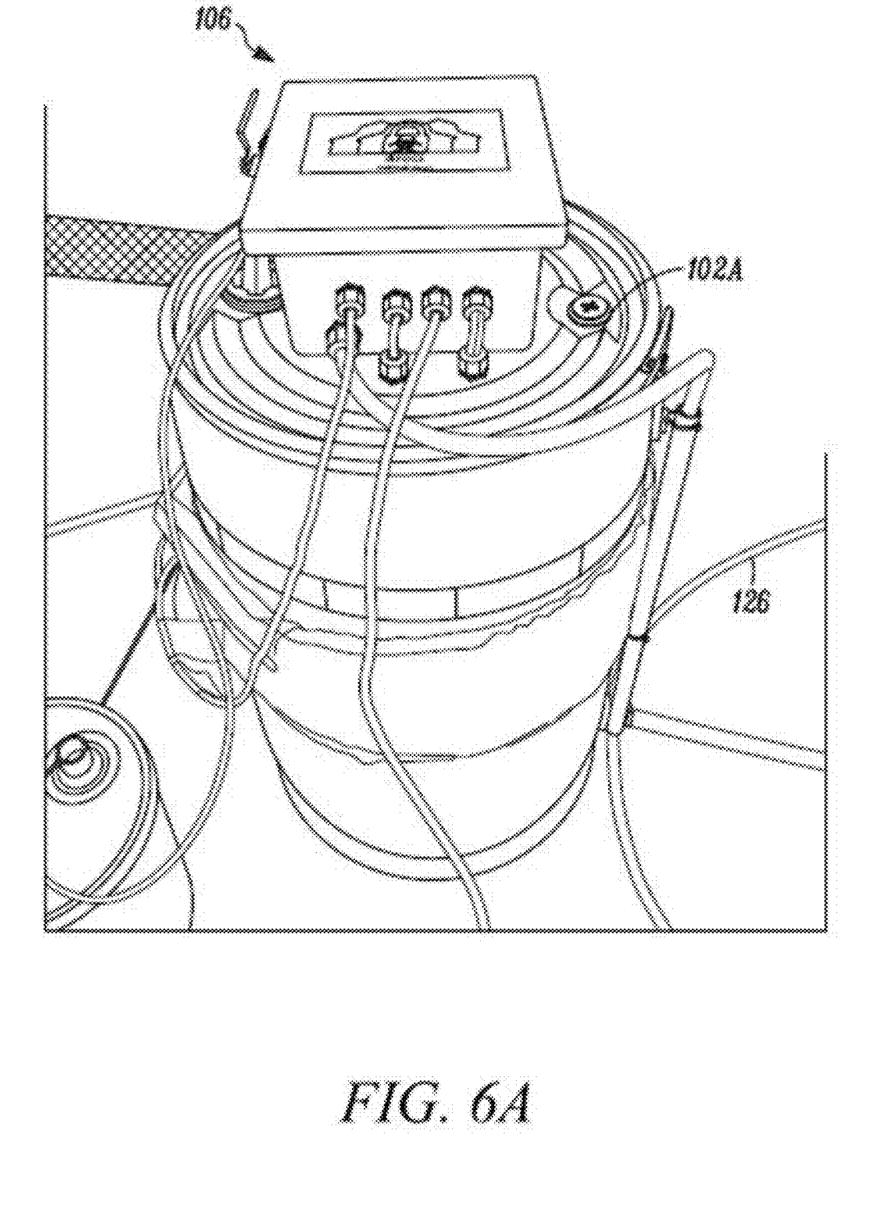
Figure 6B:
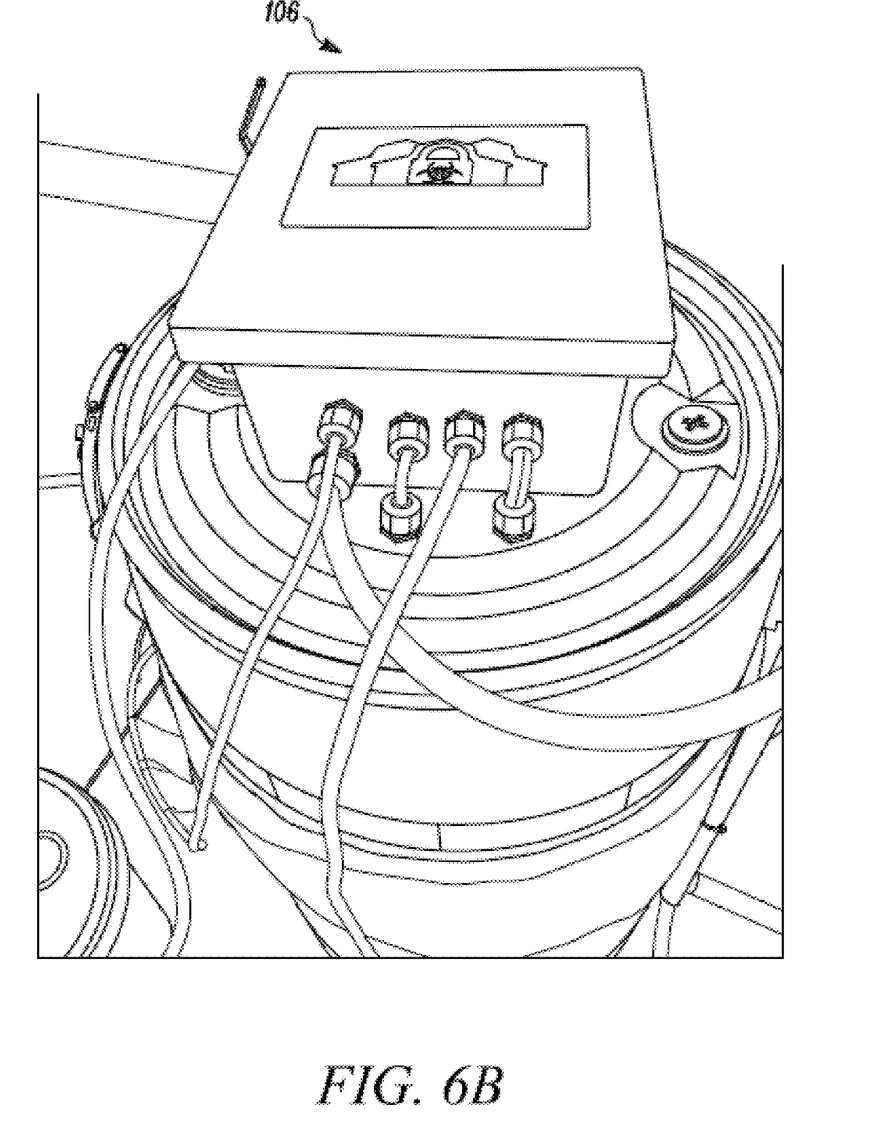
Figure 7:
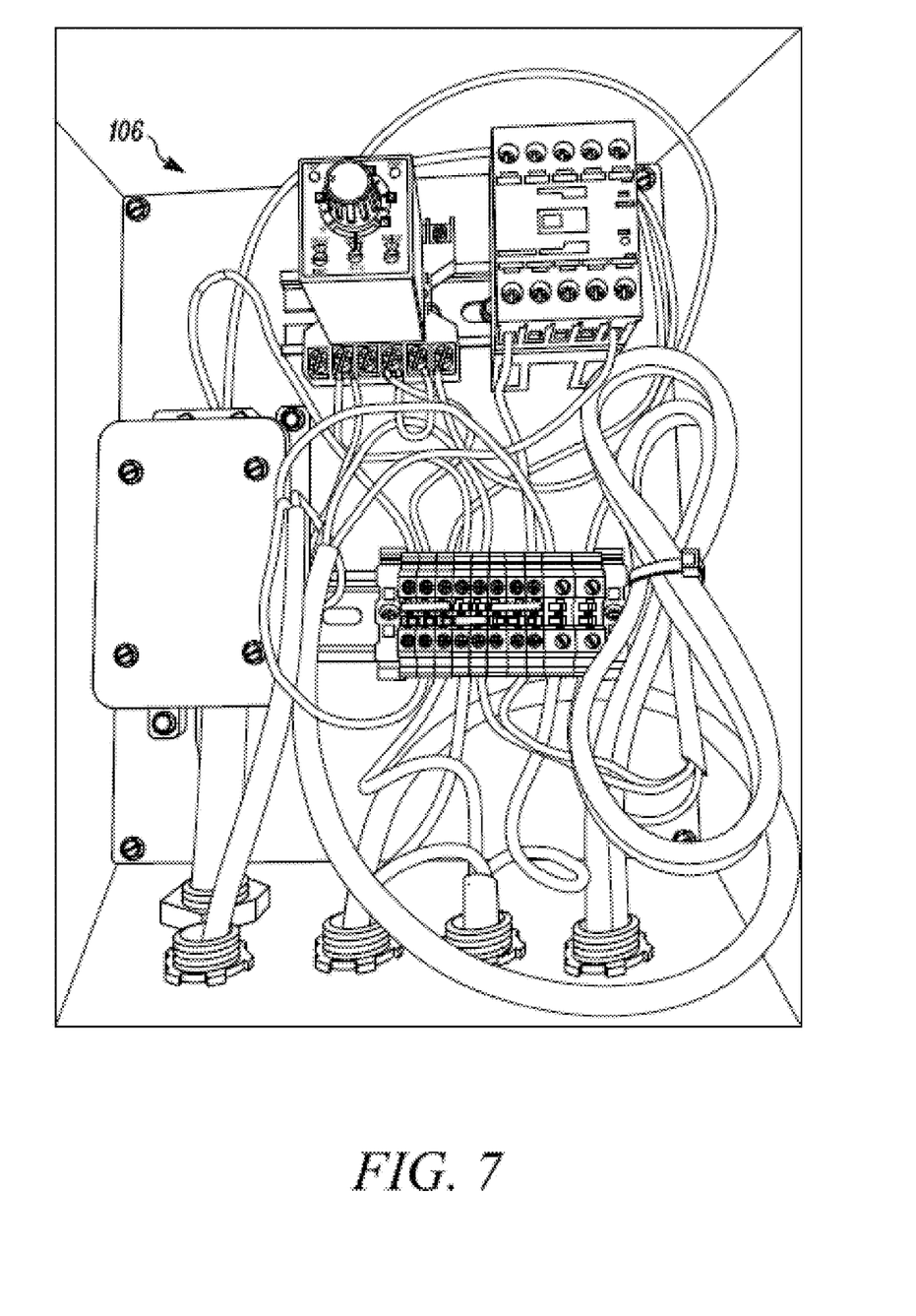

Referring to FIGS. 6A-7, in one embodiment, the control assembly 106 can include a pressure pump activation trigger 126 configured to activate pressure pump 113. In one embodiment, pressure pump activation trigger 126 can incorporate an air switch, configured to activate pressure pump 113 upon being driven over by a vehicle. In other embodiments, pressure pump activation trigger 126 can be a push button activated by a user, a photo electric eye configured to activate pressure pump 113 upon the sensing of a vehicle, or a combination of the above mentioned triggers.

In one embodiment, the control system can further include a pressure pump deactivation trigger configured to deactivate pressure pump 113. In one embodiment, the pressure pump deactivation trigger can be a timer configured to deactivate pressure pump 113 upon the passage of predetermined amount of time after the triggering of pressure pump activation trigger. In other embodiments, pressure pump activation trigger can be a photo electric eye configured to deactivate pressure pump 113 upon ceasing to sense a vehicle, or a combination of the above mentioned triggers. In one embodiment, the control assembly 106 includes a countdown timer visible to the driver, thereby enabling the driver to adjust the speed of their vehicle to ensure substantially equal disinfectant application over the entire length of the vehicle.

In one embodiment, the automatic vehicle disinfection station 200 can further include a light to selectively illuminate the vehicle disinfection station 200. In some embodiments, the light is turned on and off by the one or more pressure pump activation and or deactivation triggers 122, such as an air switch, push button start, photo electric eye, timer, or any combination thereof. In one embodiment, the light can be positioned on top of the control assembly 106. In one embodiment, the light can include a countdown timer displaying the number of seconds remaining for the application of disinfectant, and can be configured to be visible to the driver, so as to enable the driver to adjust the speed of their vehicle to ensure substantially equal disinfectant application over the entire length of the vehicle.

In operation, the automatic vehicle disinfection system 100 can be packaged and shipped within the reservoir of the resilient drums 102A/B, such that the resilient drums 102A/B contain all of the various components disclosed and described herein. The compact packaging of the automatic vehicle disinfection system 100 serves to significantly reduce the costs associated with shipping.

Prior to placement, a location for positioning of the vehicle disinfection station 100 can be determined. The one or more resilient drums 102 can be transported to the location, and laid out in the appropriate configuration for assembly. The components of the disinfectant supply system 104 and the control assembly 106 can be installed and fitted within the one or more vehicle wash ramps 102 and/or riser tubes 114, 118 as required. In particular, the at least one cross tube 116 can be coupled to the riser tubes 114, 118. In some embodiments, several cross tubes 116 are required to cross the span of the roadway. In such embodiments, the cross tubes 116 can be coupled together via one or more quick disconnects 122. One or more quick disconnect 122 can also be used to couple the cross tubes 116 with the riser tubes 114, 118.

The one or more pressure pump activation trigger 122 can be installed and/or positioned appropriately in front of or behind the vehicle disinfection station. Tank 105 can be filled with disinfectant, and the vehicle disinfection station 100 can be coupled to an electrical and/or water supply.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

What is claimed is:

1. An automatic vehicle disinfection system for promoting bio-security through application of disinfectant to a vehicle transiting to and from an agricultural site or the like, the disinfection system comprising:
    a first resilient drum including a first riser tube having one or more disinfectant dispensing nozzles, the first resilient drum further including a disinfectant reservoir;
    a second resilient drum including a second riser tube having one or more disinfectant dispensing nozzles;
    a resilient cross-tube fluidly connecting the first riser tube with the second riser tube, the cross tube including a central spray unit having one or more disinfectant dispensing nozzles;
    a pressure pump configured to pump disinfectant from the disinfectant reservoir to the disinfectant dispensing nozzles; and
    a control assembly including a pressure pump activation trigger configured to activate the pressure pump;
    wherein the pressure pump and the control assembly are operably coupled to at least one of the first resilient drum and the second resilient drum.

2. The automatic vehicle disinfection system of claim 1, wherein the disinfectant reservoir includes a heater configured to promote a free flow of disinfectant and inhibit the disinfectant from freezing and/or from having ice crystals formed therein.

3. The automatic vehicle disinfection system of claim 1, wherein the cross-tube is interchangeable via one or more quick disconnects, so as to accommodate vehicles of a range of widths and sizes.

4. The automatic vehicle disinfection system of claim 1, wherein the pair of resilient drums are configured to temporarily deform and resume their original shape after being impacted by an external force.

5. The automatic vehicle disinfection system of claim 1, wherein the pair of resilient drums are configured to resist damage when impacted by a vehicle.

6. The automatic vehicle disinfection system of claim 1, wherein the pair of resilient drums are constructed of at least one of resilient rubber, plastic, or a combination thereof.

7. The automatic vehicle disinfection system of claim 1, wherein at least one of the first riser tube, second riser tube, and/or resilient cross-tube is constructed of a resilient hose member configured to deform upon the application of stress.

8. The automatic vehicle disinfection system of claim 1, wherein the automatic vehicle disinfection system is configured to be disassembled and packed into an interior of at least one of the pair of resilient drums.

9. An automatic vehicle disinfection system for promoting bio-security through application of disinfectant to a vehicle, the disinfection system comprising:
    a resilient drum including a first riser tube having one or more disinfectant dispensing nozzles, the resilient drum further including a disinfectant reservoir;
    a second riser tube having one or more disinfectant dispensing nozzles; and
    a cross-tube fluidly connecting the first riser tube with the second riser tube.

10. The automatic vehicle disinfection system of claim 9, further comprising a pressure pump configured to pump disinfectant from the disinfectant reservoir.

11. The automatic vehicle disinfection system of claim 9, further comprising a pressure pump activation trigger configured to initiate application of the disinfectant to the vehicle.

12. The automatic vehicle disinfection system of claim 9, wherein the cross-tube is interchangeable via one or more quick disconnects.

13. The automatic vehicle disinfection system of claim 9, wherein at least one of the first riser tube, second riser tube, and/or cross-tube is constructed of a resilient hose member configured to deform upon the application of stress.

14. The automatic vehicle disinfection system of claim 9, wherein the pair of resilient drums are configured to temporarily deform and resume their original shape after experiencing an external force.

15. The automatic vehicle disinfection system of claim 9, wherein the automatic vehicle disinfection system is configured to be disassembled and packed into an interior of at least one of the pair of resilient drums.

\* \* \* \* \*